United States Patent [19]

Ferrando et al.

[11] Patent Number: 4,645,493
[45] Date of Patent: Feb. 24, 1987

[54] CATHETER FOR MEDICAL-SURGICAL APPLICATION

[75] Inventors: Ugo Ferrando; Giovanni Gardi; Giustino Pagliano, all of Turin, Italy

[73] Assignee: N.U.S. S.r.l., Turin, Italy

[21] Appl. No.: 790,785

[22] Filed: Oct. 21, 1985

Related U.S. Application Data

[63] Continuation of Ser. No. 565,884, Dec. 27, 1983, abandoned.

[30] Foreign Application Priority Data

Jan. 7, 1983 [IT] Italy ............................. 52816/83[U]

[51] Int. Cl.$^4$ ............................................ A61M 25/00
[52] U.S. Cl. ..................................... 604/174; 604/280
[58] Field of Search ................ 604/280, 282, 104–106, 604/247, 250, 264, 9

[56] References Cited

U.S. PATENT DOCUMENTS

| | | | |
|---|---|---|---|
| Re. 27,310 | 3/1972 | Hakim | 604/268 |
| 3,626,950 | 12/1971 | Schulte | 604/268 |
| 3,788,327 | 1/1974 | Donowitz et al. | 604/9 X |
| 3,896,804 | 7/1975 | Ekbladh et al. | 604/280 X |
| 3,938,539 | 2/1976 | Gibbons | 604/282 X |
| 4,475,898 | 10/1984 | Brodnar et al. | 604/9 |

*Primary Examiner*—Stephen C. Pellegrino
*Attorney, Agent, or Firm*—Young & Thompson

[57] ABSTRACT

A catether prosthesis for medical-surgical application, of silicone material, is manufactured by mass-production, and its positioning in the patient is made rapid, easy and painless by inserting into its stem an insert, also of silicone material, which is removed by withdrawing it after cutting the stem to the length required to be inserted into the ureter; said stem, which is of considerable length, it provided with density distributed drainage holes, and with tongues for locking it in position.

3 Claims, 4 Drawing Figures

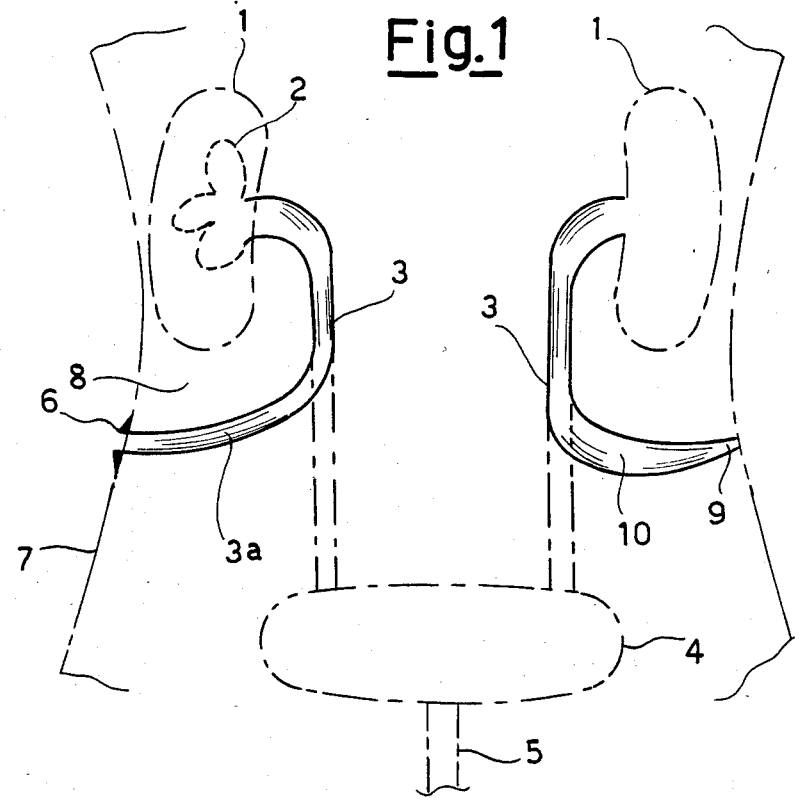
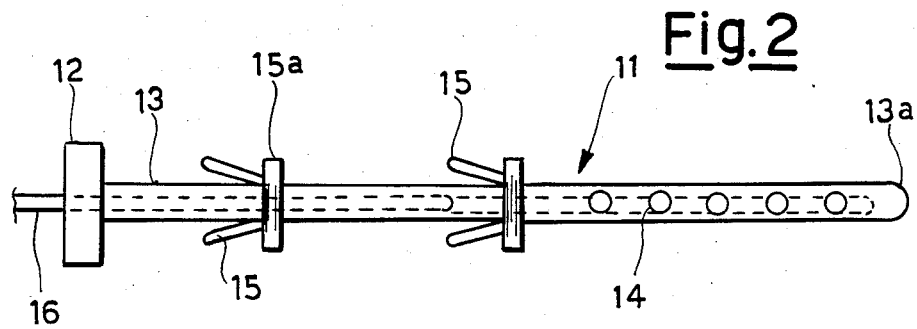

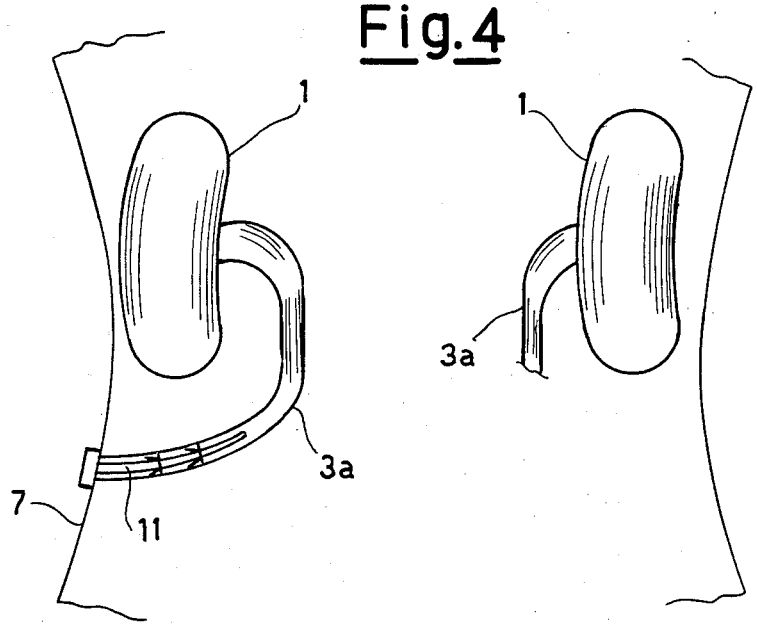
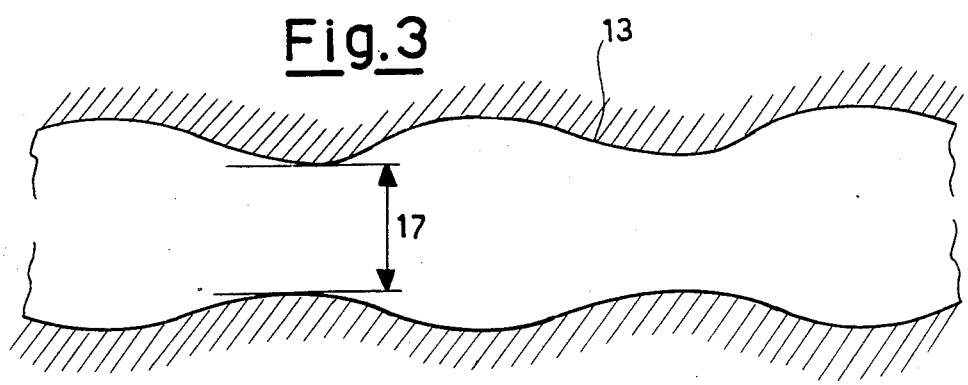

CATHETER FOR MEDICAL-SURGICAL APPLICATION

This application is a continuation of application Ser. No. 565,884, filed Dec. 27, 1983, now abandoned.

DESCRIPTION

This invention relates to a catheter for particular application to the ureteral organs of the patient, and more specifically relates to its construction and operation.

The ureter is known to be the organ which connects the patient's kidney to the bladder, from which the physiological liquid is expelled through the urethra, but it is likewise known that said bladder can become deactivated due to various impediments such as adverse tumoral growths, with the result that the ureter has to be placed in a new determined position, with its opening at the skin, ie the classical surgical operation known as ureterocutaneostomy has to be carried out.

However, said operation can lead to various serious problems, such as possible reduction in the cross-section of the pair of ureters, or in contrast their enlargement, to lead to abnormal renal pressure and serious consequences for the patient, due to the inefficient discharge of urine, accompanied by possible stagnation in the duct, which can lead to infection and, as a consequence, extremely compromised kidney function.

Various types of a valid and functional element known as a prosthesis have been designed, including by the present applicant, for obviating these serious drawbacks, it being inserted into the ureter to allow liquid expulsion, so reducing the aforesaid serious drawbacks.

The object of the present invention is to improve the performance of said prosthesis, by particular and detailed technical means, such as an increase in size, combined with a specific functional structure.

A further object is to transform its individual artesan production into industrial mass-production, to facilitate and quicken its insertion into the patient, and to provide improved operation which lasts with time, to thus also attain an economical advantage, especially in terms of its manufacture, in which costs are reduced and profits are thus made commercially competitive.

These objects and advantages, together with others which will be apparent from the detailed description given hereinafter, are attained by a catheter prosthesis for medical-surgical application, of silicone material, the main characteristic of which is its manufacture by mass-production, and which can be positioned rapidly, easily and painlessly in the patient by inserting into its stem an insert, which is also of silicone material, and which can be removed by withdrawing it after cutting the stem to the length required to be inserted into the ureter, said stem, which is of considerable length, being provided with numerous drainage holes, and with tongues for locking it in position.

A preferred embodiment of the invention is described hereinafter by way of non-limiting example with reference to the accompanying drawings in which:

FIG. 1 is a diagrammatic view of that sector of the human body concerned with the insertion of the catheter element according to the invention;

FIG. 2 is an external front view of the catheter according to the invention, to an enlarged scale;

FIG. 3 is an explanational detail of FIG. 2, to a further enlarged scale;

FIG. 4 is similar to FIG. 1, but showing the insertion of the new prosthesis.

In the aforesaid figures, the reference numeral 1 indicates diagrammatically the two human kidneys, from each of their internal calices 2 there extending the ureter 3 connected to the bladder 4, from which there extends the urethra 5 for expelling the physiological liquid (see the dashed and dotted lines in FIG. 1).

When the serious need arises to suppress the bladder 3 because of its malformation or because of tumoral impediments, a surgical operation known as anastomosis is carried out in which the ureters are removed from the bladder 4 and then made to take an arcuate path 3a so that they open at 6 at the skin 7, by passing through the muscular fascia 8 (see continuous lines in FIG. 1).

With the ureter 3a in this new position, it can become constricted downstream at 9, or become enlarged upstream at 10, to thus lead to a stagnant build-up of urine due to its imperfect expulsion, with a dangerous increase in renal pressure and serious consequences for the patient.

To obviate these drawbacks, the catheter 11 is inserted into the ureter 3a, said catheter being constructed of silicone material and possessing specific inventive characteristics, particularly with regard to its configuration and dimensions (see FIG. 4).

In detail, it comprises a head 12 having a value (not shown), from which extends the cylindrical stem 13, which is of considerable length, has its free end radiused at 13a, is internally bored axially, and is provided with numerous diametrical through holes 14 (see FIG. 2).

Moreover, on said stem 13 there are mounted pairs of tongues 15 of silicone material, which oppose each other on a diametrical axis and are configured with arcuate profiles, so that no sharp edges are present.

The positioning of the catheter 11, which is already facilitated by the softeness of its material, is made more rapid by the insertion of an insert 16, able when inserted to provide the stem 13 with a certain rigidity, thus facilitating its introduction.

Because the catheter 11 is constructed to a standardised size in order to attain the high industrial production according to the invention, said insert or rod 16, again of silicone material, is usefully provided with measurement graduations, so that the surgeon is able to visibly read-off the length necessary for the patient's organ, and thus after inserting the insert he cuts the stem 13 at the exact required length, and subsequently withdraws said insert 16.

The tongues 15 are joined to the stem 13 by way of a ring 15a, using thermo-welding, which is also used for joining the head 12, thus advantageously providing a further positive characteristic, namely a single and common type of joint for said components.

A further characteristic is that the catheter 11 cannot become displaced from its operating position, by virtue of the presence of said tongues 15 which provide a reliable locking action for any type and density of the patient's muscular fascia 8, and is also painless because of the softness of the material and the curved profile of said tongues.

Furthermore, the densely distributed holes 14 ensure optimum drainage of urine from the ureter 3a and its discharge through the internal bore of the stem 13 and thus through the head 12, for collection in a container (not shown) which is itself joined to said head, this latter also providing a useful stop action against the skin, so as to position the prosthesis.

During said flow of fluid, the presence of the tongues 15 means that by virtue of their being positionally fixed to the relative ring 15a on the stem 13, the inner surface of this latter, constricted by the rings is a, assumes an undulating axial profile, which in section is diametrically tapered at 17, to thus result in an increase in the velocity of the flowing fluid by virtue of the corresponding physical principle. This has positive results on the expulsion function according to the invention, which means that the tongues 15 have a definite double purpose, namely the said improved urine discharge, and the effective locking of the catheter in the ureter 3a (see FIG. 3).

The functional validity of this important and essential catheter prosthesis is apparent from the aforegoing, it being also of easy and rapid industrial manufacture, and excellent to use.

Within the principle of the invention, its practical embodiments can undergo wide modifications relative to that described by way of non-limiting example, in order to acquire increased functionality and economy, but without exceeding the scope of the present invention as protected by the following claims.

We claim:

1. A catheter for medical-surgical application, constructed of silicone material, comprising a hollow stem closed at one end and having an annular head at the other end, the stem having spaced along its length no more than two pairs of tongues also of silicone material for locking the catheter in position, each said pair comprising two diametrically opposed tongues that are inclined away from said closed end and have rounded free ends, and a plurality of drainage holes spaced apart lengthwise of the catheter and disposed between said closed end and said pair of tongues closest to said closed end, each said pair of tongues being secured to a ring which in turn is secured to the exterior of the hollow stem, each said ring being devoid of tongues between said two diametrically opposed tongues on each ring.

2. A catheter as claimed in claim 1, in combination with a silicone rod that fits within the catheter to assist in insertion of the catheter.

3. A catheter as claimed in claim 1, there being two said rings spaced apart lengthwise of said hollow stem.

* * * * *